United States Patent [19]

Matsumoto et al.

[11] 4,341,784
[45] Jul. 27, 1982

[54] NAPHTHYRIDINE DERIVATIVES

[75] Inventors: Jun-ichi Matsumoto, Ikoma; Yoshiyuki Takase, Amagasaki; Yoshiro Nishimura, Neyagawa, all of Japan

[73] Assignees: Dainippon Pharmaceutical Co., Ltd., Osaka, Japan; Laboratoire Roger Bellon, Neuilly sur Seine, France

[21] Appl. No.: 187,081

[22] Filed: Sep. 15, 1980

[30] Foreign Application Priority Data

Sep. 28, 1979 [JP] Japan ................... 54-126223

[51] Int. Cl.³ .................. A61K 31/44; C07D 471/04
[52] U.S. Cl. ................................. 424/256; 546/123
[58] Field of Search ................ 546/123; 424/263, 256

[56] References Cited

U.S. PATENT DOCUMENTS

| | | | |
|---|---|---|---|
| 3,149,104 | 9/1964 | Lesher et al. | 544/362 |
| 3,673,193 | 6/1972 | Lesher et al. | 546/123 |
| 3,786,043 | 1/1974 | Brundage et al. | 546/123 |
| 4,024,255 | 5/1977 | Ellis et al. | 546/123 |
| 4,195,087 | 3/1980 | Simonovitch | 546/123 |

FOREIGN PATENT DOCUMENTS

| | | | |
|---|---|---|---|
| 2607012 | 8/1977 | Fed. Rep. of Germany | 546/123 |
| 49-126697 | 12/1974 | Japan | 546/123 |
| 50-111080 | 9/1975 | Japan | 546/153 |
| 54-03095 | 11/1979 | Japan | 546/123 |
| 7601632 | 2/1975 | Netherlands | 546/123 |

OTHER PUBLICATIONS

Nishigaki et al., Chem. Abst., 87:23104x.
Susuki et al., Chem. Abst., 91:56865g, same as Yakugaku Zasshi 1979, 99(2), 155–164.

*Primary Examiner*—Jane T. Fan
*Attorney, Agent, or Firm*—Wenderoth, Lind & Ponack

[57] ABSTRACT

The present invention provides a 1,8-naphthyridine compound of the formula

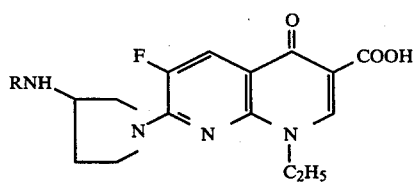

wherein
R is hydrogen, methyl, ethyl or propyl, and a non-toxic pharmaceutically acceptable salt thereof, and a process for preparing a 1,8-naphthyridine compound of the above formula which comprises
(A) reacting a compound of the formula

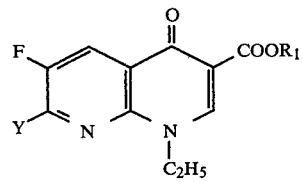

wherein
Y is halogen, lower alkoxy, lower alkylthio, lower alkylsulfinyl, lower alkylsulfonyl, lower alkylsulfonyloxy or arylsulfonyloxy, and $R_1$ is hydrogen or lower alkyl,
with a compound of the formula

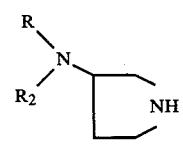

wherein $R_2$ is hydrogen or a protective group for the amino group, and R is as defined above,
and when a reaction product in which $R_1$ is lower alkyl and/or $R_2$ is the amino protective group is obtained, treating it with an acid or base, and/or reductively cleaving it,
(B) decomposing a compound of the formula

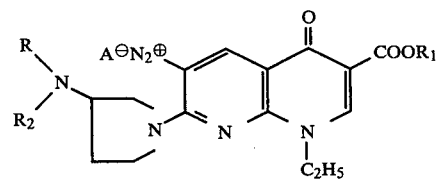

wherein $A \ominus$ is a fluorine-containing anion, and $R_1$ and $R_2$ are as defined above,
and when a reaction product in which $R_1$ is lower alkyl and/or $R_2$ is the amino protective group is obtained, treating it with an acid or base, and/or reductively cleaving it,
(C) treating a compound of the formula

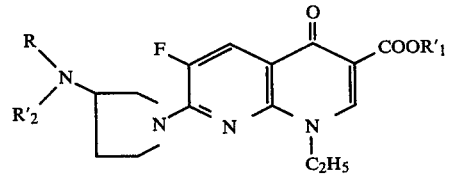

wherein $R'_1$ is hydrogen or lower alkyl, $R'_2$ is hydrogen or a protective group for the amino group, provided that $R'_1$ and $R'_2$ are not hydrogen atoms at the same time, and R is as defined above,
with an acid or base, and/or reductively cleaving it, and optionally converting the resulting compound to a non-toxic pharmaceutically acceptable salt thereof.
The 1,8-naphthyridine compound is useful as an antibacterial agent.

7 Claims, No Drawings

NAPHTHYRIDINE DERIVATIVES

This invention relates to novel naphthyridine derivatives having high antibacterial activities and processes for preparing said novel compounds.

The present invention provides compounds of the following formula

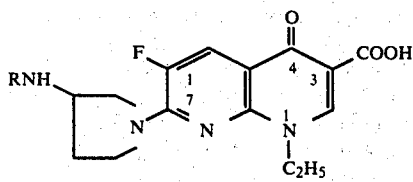

wherein R is hydrogen, methyl, ethyl or propyl and nontoxic pharmaceutically acceptable salts thereof.

The salts of the naphthyridine compounds [I] are formed between the naphthyridine compounds [I] and acids or bases. The acids may be various inorganic and organic acids, and examples of suitable acids are hydrochloric acid, acetic acid, lactic acid, succinic acid, lactobionic acid, and methanesulfonic acid. The bases may be any inorganic or organic bases capable of forming salts with the carboxyl group of the compounds [I], and examples of suitable bases are metal hydroxides such as sodium or potassium hydroxide, and metal carbonates such as sodium or potassium carbonate.

Especially preferred salts of the compounds [I] are the hydrochlorides or methanesulfonates.

Depending upon the conditions, the naphthyridine compounds [I] may form as hydrates. These hydrates are also embraced by the naphthyridine compounds of the present invention which are represented by formula [I].

It is an object of this invention to provide novel naphthyridine compounds having high antibacterial activities against Gram-positive bacteria and Gram-negative bacteria including *Pseudomonas aeruginosa*, and processes for preparing these novel compounds.

Another object of this invention is to provide a pharmaceutical composition containing such a novel naphthyridine compound.

These and other objects of this invention become apparent from the following description.

The compounds of this invention represented by formula [I] include the following.

7-(3-Amino-1-pyrrolidinyl)-1-ethyl-6-fluoro-1,4-dihydro-4-oxo-1,8-naphthyridine-3-carboxylic acid, 1-Ethyl-6-fluoro-1,4-dihydro-7-(3-methylamino-1-pyrrolidinyl)-4-oxo-1,8-naphthylidine-3-carboxylic acid, 1-Ethyl-7-(3-ethylamino-1-pyrrolidinyl)-6-fluoro-1,4-dihydro-4-oxo-1,8-naphthylidine-3-carboxylic acid, 1-Ethyl-6-fluoro-1,4-dihydro-4-oxo-7-(3-isopropylamino-1-pyrrolidinyl)-1,8-naphthylidine-3-carboxylic acid, 1-Ethyl-6-fluoro-1,4-dihydro-4-oxo-7-(3-n-propylamino-1-pyrrolidinyl)-1,8-naphthylidine-3-carboxylic acid, and the salts of the above compounds, such as their hydrochlorides and methanesulfontes. Of these, the following compounds are preferred.

7-(3-Amino-1-pyrrolidinyl)-1-ethyl-6-fluoro-1,4-dihydro-4-oxo-1,8-naphthyridine-3-carboxylic acid of the following formula, and its hydrochloride (to be referred to as Compound 1)

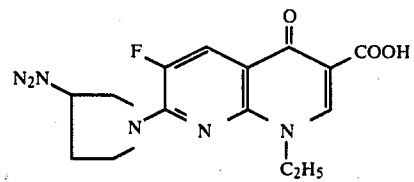

1-Ethyl-6-fluoro-1,4-dihydro-7-(3-methylamino-1-pyrrolidinyl)-4-oxo-1,8-naphthyridine-3-carboxylic acid of the following formula, and its hydrochloride (to be referred to as Compound 2)

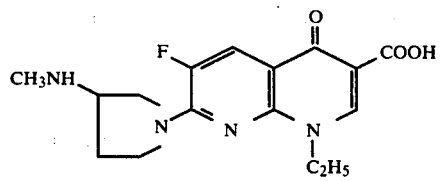

The compounds of this invention show excellent antibacterial activities and a broad antibacterial spectrum in in vitro tests. Furthermore, these compounds show an excellent infection-defensing effect in vivo on systemic infections caused by Gram-positive and Gram-negative bacteria including *Pseudomonas aeruginosa* because their strong antibacterial activities in vitro are well reflected.

While the compounds of this invention show such superior antibacterial activities, their acute oral toxicity (especially the acute oral toxicities of the Compounds 1 and 2) is very weak. It has also been found that Compound 2 has lower acute toxicity in intervenous injection than Compound 1.

The compounds of this invention are especially useful as oral antibacterial agents for systemic infections.

Japanese Laid-Open Patent Publication No. 126697/74 [the abstract of which is disclosed in Central Patents Index published by Derwent Publications Ltd., under Accession No. (to be abbreviated Der. No.) 2017 W/12] discloses 6-unsubstituted 1,8-naphthyridine derivatives of the following formula

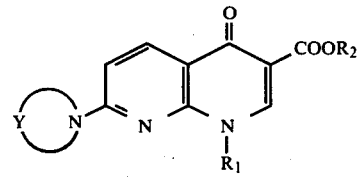

wherein Y is alkylene having 4 to 6 carbon atoms which may be substituted by hydroxy or lower alkanoyloxy; or alkylene having 4 to 5 carbon atoms which are interrupted by oxygen or =N—R (wherein R is hydrogen, lower alkyl, lower alkanoyl or aralkyl), and each of $R_1$ and $R_2$ is hydrogen or lower alkyl.

As is clearly seen from the above formula, the 1,8-naphthyridine derivatives disclosed in the Japanese Publication have no substituent at the 6-position of the naphthyridine nucleus.

Among the compounds disclosed in this Japanese Publication, the compound of the following formula

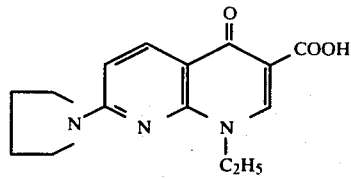

(to be sometimes referred to as Compound A) most resembles structurally the compounds of this invention in that the 7-position is substituted by a pyrrolidinyl group.

YAKUGAKU ZASSHI (JAPAN), volume 99, No. 2, pp. 155–164 (February 1979) describes various 1,8-naphthyridine derivatives. Among these compounds, the 6-chloro-1,8-naphthyridine compound of the following formula

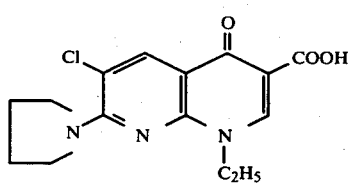

(to be sometimes referred to as Compound B) most resembles structurally to the compounds of this invention in that the 6-position is substituted by halogen and the 7-position is substituted by a pyrrolidinyl group.

The compounds of this invention, however, have much higher antibacterial activities than the structurally similar known compounds A and B, as will be shown in Examples given hereinbelow.

The compounds of formula [I] and their salts are prepared by carrying out at least one of the following processes A to C.

Process A: Displacement by pyrrolidine derivatives

The compounds of formula [I] are prepared by reacting a compound of the following formula

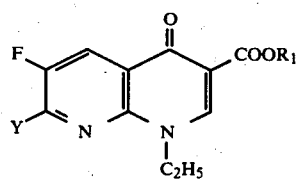 (a)

wherein
Y is halogen, lower alkyloxy, lower alkylthio, lower alkylsulfinyl, lower alkylsulfonyl, lower alkylsulfonyloxy or arylsulfonyloxy, and
$R_1$ is hydrogen or lower alkyl,
with a compound of the following formula

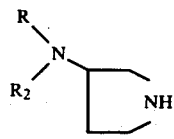 (b)

wherein
R is the same as defined in formula [I], and
$R_2$ is hydrogen or a protective group for the amino group,
and when a reaction product in which $R_1$ is lower alkyl and/or $R_2$ is a protective group for the amino group is obtained, treating the reaction product with an acid or base and/or reductively cleaving the reaction product to convert $R_1$ and $R_2$ to a hydrogen atom.

The protective group for the amino group expressed by $R_2$ in formula (b) denotes a group which can be split off by treatment with a base or acid or by reductive cleavage. Examples of the protective group $R_2$ capable of being eliminated by treatment with acids or bases include acyl groups such as formyl, acetyl, trifluoroacetyl, benzyloxycarbonyl, t-butoxycarbonyl, p-methoxybenzyloxycarbonyl, vinyloxycarbonyl, ethoxycarbonyl and beta-(p-toluenesulfonyl)ethoxycarbonyl; tri-lower alkyl silyl groups such as trimethylsilyl and t-butyldimethylsilyl; halogenoethoxycarbonyl groups such as $\beta,\beta,\beta$-trichloroethoxycarbonyl and $\beta$-iodoethoxycarbonyl; o-nitrophenylsulfenyl; trityl; tetrahydropyranyl; and diphenylphosphinyl.

Examples of the protective group $R_2$ capable of being eliminated by reductive cleavage include arylsulfonyl groups such as p-toluenesulfonyl; methyl groups substituted by phenyl or benzyloxy such as benzyl, trityl or benzyloxymethyl; arylmethylcarbonyl groups such as benzyloxycarbonyl or p-methoxybenzyloxycarbonyl.

The compounds of formula (a) are novel compounds, and may be prepared from known compounds of the following formula

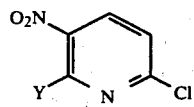

wherein Y is as defined hereinabove, by, for example, following the Reaction Scheme 1 of Norwegian Laid-Open Patent Publication No. 7902760; or by the method described in Reference Example 1 given hereinbelow.

The above displacement reaction is performed by reacting the compounds (a) and (b) with or without a solvent, if desired, in a sealed reaction vessel. It is preferred to perform the reaction in the presence of a base, as an acid-acceptor, such as sodium bicarbonate, sodium carbonate, potassium carbonate, triethylamine, pyridine or picoline. Usually, the compounds (a) and (b) are used in stoichiometric amounts. Furthermore, the compound (b) may be used in excess to make it serve also as an acid-acceptor.

The preferred reaction temperature is in the range from about 20° C. to about 150° C.

The solvent used in this reaction should be selected according to the properties of the starting materials to be used. Examples of the solvent are aliphatic alcohols such as ethanol or propanol; aromatic hydrocarbons such as benzene or toluene; haloalkanes such as dichloroethane or chloroform; ethers such as tetrahydrofuran, dioxane or diphenyl ether; acetonitrile; dimethyl sulfoxide; dimethylformamide; and water. They may be used either alone or in combination with each other.

According to this displacement reaction, there is formed a compound resulting from substitution of the compound (b) for the substituent Y at the 7-position of the compound (a). Sometimes a reaction product in which $R_1$ is hydrogen forms a salt with the acid-acceptor in the reaction system.

When $R_1$ is a lower alkyl group and/or $R_2$ is a protective group for the amino group, the reaction product of the displacement reaction is then treated with an acid or base in the presence or absence of water, and/or reductively deprotected to convert $R_1$ and/or $R_2$ to a hydrogen atom.

The operation of eliminating the protective group may be applied to the reaction mixture obtained after the displacement reaction or to the product isolated from the reaction mixture.

The treatment with an acid or base is carried out by contacting the displacement reaction product with an acid or base at a temperature of about 0° C. to about 150° C.

Examples of the acid are inorganic acids such as hydrochloric acid, hydrobromic acid, sulfuric acid and phosphoric acid, organic acids such as acetic acid, trifluoroacetic acid, formic acid and toluenesulfonic acid; and Lewis acids such as boron trifluoride and aluminum chloride. Examples of the base are alkali metal hydroxides such as sodium hydroxide and barium hydroxide; alkali metal carbonates such as sodium carbonate and potassium carbonate; alkali metal alkoxides such as sodium methoxide and sodium ethoxide; sodium acetate; sodium hydride; and zinc.

The treatment with an acid or base is carried out in the presence or absence of water depending upon the type of the amino protective group $R_2$. For example, this treatment is carried out generally in the presence of water when $R_2$ is an acyl group such as formyl, acetyl, trifluoroacetyl, benzyloxycarbonyl, t-butoxycarbonyl, p-methoxybenzyloxycarbonyl, vinyloxycarbonyl or ethoxycarbonyl; a tri-lower alkyl silyl group such as trimethylsilyl or t-butyldimethylsilyl; trityl; or tetrahydropyranyl.

The solvent is usually water, but depending upon the properties of the resulting compound, a solvent such as ethanol, dioxane, ethyleneglycol dimethyl ether, benzene or acetic acid together with water may be used. The reaction temperature may be usually about 0° C. to about 150° C., preferably about 30° C. to about 100° C.

When $R_2$ is $\beta$-(p-toluenesulfonyl)ethoxycarbonyl or o-nitrophenylsulfenyl, $\beta,\beta,\beta$-trichloroethoxycarbonyl, $\beta$-iodoethoxycarbonyl or diphenylphosphinyl, the treatment with an acid or base is carried out generally in the absence of water. This reaction may be carried out, for example, by contacting a compound in which $R_2$ is $\beta$-(p-toluenesulfonyl)ethoxycarbonyl with an alkali metal alkoxide such as sodium methoxide or sodium ethoxide in an alcohol such as methanol or ethanol at 0° C. to 80° C. When $R_2$ is o-nitrophenylsulfenyl, this treatment is carried out by contacting the aforesaid compound with glacial acetic acid at a temperature of 0° C. to 80° C. When $R_2$ is $\beta,\beta,\beta$-trichloroethoxycarbonyl or $\beta$-iodoethoxycarbonyl, the reaction is also carried out by treating the aforesaid compound with zinc dust in acetic acid or methanol at a temperature of 0° C. to 80° C. In the acid or base treatment, too, when $R_1$ is lower alkyl, $R_1$ may be converted to a hydrogen atom by adding water to the reaction system and heating it at about 30 to about 100° C.

According to the acid or base treatment, $R_1$ and/or $R_2$ in the displacement reaction product in which $R_1$ is lower alkyl and/or $R_2$ is an amino protective group capable of being split off by the acid or base treatment can be advantageously eliminated to afford the 1,8-naphthyridine compound of this invention expressed by formula [I]. The resulting compound is obtained as a free compound or at times, as an addition salt with the base or acid used in the elimination of $R_1$ and/or $R_2$.

The reductive cleavage is generally carried out in the following manner although the reaction conditions differ depending upon the type of the protective group $R_2$.

For example, when $R_2$ is a methyl group substituted by phenyl or benzyloxy (e.g., benzyl, trityl or benzyloxymethyl) or an arylmethoxycarbonyl group such as benzyloxycarbonyl or p-methoxybenzyloxycarbonyl, the reducing reaction is carried out by treating the compound with a hydrogen stream in an inert solvent in the presence of a catalyst such as platinum, palladium, Raney nickel or the like.

The catalytic hydrogenolysis proceeds at room temperature. If desired, however, it may be carried out at an elevated temperature of up to 60° C. Suitable solvents for this reaction are ethylene glycol, dioxane, dimethylformamide, ethanol, and acetic acid.

When $R_2$ is a benzyl, trityl, benzyloxycarbonyl or p-toluenesulfonyl group, such a group can be split off with metallic sodium in liquid ammonia, usually at $-50°$ C. to $-20°$ C.

Hence, according to this reductive cleavage, the 1,8-naphthyridine compound [I] of this invention is obtained from the displacement reaction product in which $R_1$ is hydrogen and $R_2$ is an amino protective group capable of being split off by reductive cleavage.

As is already clear, the acid or base treatment or the reductive cleavage is properly applied to the displacement reaction product in which $R_1$ is a lower alkyl group and $R_2$ is an amino protective group, depending upon whether the amino protective group $R_2$ can be split off by the acid or base treatment or by the reductive cleavage. For example, the reaction product in which $R_1$ is lower alkyl and $R_2$ is an amino protective group capable of being split off by reductive cleavage can be firstly treated with an acid or base and then subjected to reductive cleavage, or conversely, firstly subjected to reductive cleavage and then treated with an acid or base.

Process B: Fluorination via diazonium salt

The compounds of formula [I] are also obtained by decomposing a compound of the following formula

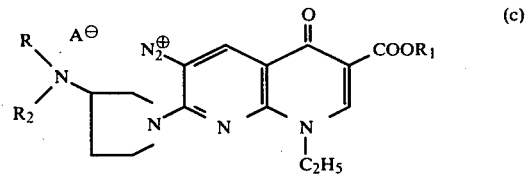

(c)

wherein $A^\ominus$ is fluorine-containing anion, and $R_1$ and $R_2$ are the same as defined above, and when a reaction product in which $R_1$ is lower alkyl and/or $R_2$ is a protective group for the amino group is obtained, treating the reaction product with an acid or base and/or reductively cleaving the reaction product to convert $R_1$ and $R_2$ to a hydrogen atom.

Examples of the fluorine-containing anion group $A^\ominus$ are $BF_4^-$, $SiF_6^{--}$, $PF_6^-$ and $SbF_6^-$.

This decomposition reaction known as the Schiemann reaction may be performed by heating the diazonium salt (c) (i.e., thermal decomposition), or by irradiating light on the diazonium salt (c) (i.e., photolytic decomposition).

The thermal decomposition is carried out by heating the diazonium salt (c) to about 50° C. to about 170° C. in a diluent or organic solvent. The diluent is used usually in an amount of 3 to 5 times the amount of the diazonium salt (c). The diluent is, for example, sand, barium sulfate or sodium fluoride. Examples of the organic solvent are those which do not participate in the present reaction, such as petroleum ether, cyclohexane, heptane, benzene, toluene, xylene, biphenyl, tetrachloromethane, ethyl acetate, chloroform, dioxane or quinoline.

The photolytic decomposition is carried out by subjecting the diazonium salt (c) to irradiation of light of wavelengths about 2500 Å to about 4000 Å at about 5° C. to about 50° C., generally at 25° C. to 35° C., in an organic solvent of the type exemplified hereinabove.

The resulting compound in which $R_1$ is lower alkyl and/or $R_2$ is an amino protective group is further subjected to the acid or base treatment and/or reduction by the same procedure as described above with regard to Process A.

The diazonium salt (c) is obtained by reacting a compound of the following formula

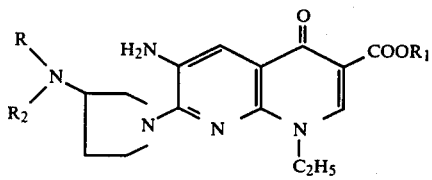

(d)

wherein R, $R_1$ and $R_2$ are the same as defined above, with a diazotizing agent in the presence of a fluorine-containing anion-yielding compound.

Examples of the diazotizing agent are nitrous acid, nitrites such as sodium nitrite, organic nitrous acid derivatives such as isoamyl nitrite, and nitrosylsulfuric acid. Examples of the fluorine-containing anion-yielding compound include acids or the salts thereof, such as $HBF_4$, $H_2SiF_6$, $HPF_6$, and $HSbF_6$.

This reaction is carried out by stirring the compound (d) and the diazotizing agent under cooling in water, an organic solvent or a mixture thereof with water in the presence of the fluorine-containing anion-yielding compound. The amount of the fluorine-containing anion-yielding compound required for the reaction is usually 3.5 to 5 equivalents to the compound (d), and the diazotizing agent is used in slight excess to the compound (d). When an inorganic agent such as sodium nitrite or nitrosylsulfuric acid is used as the diazotizing agent, this diazotization reaction is carried out in aqueous solution. When isoamyl nitrite is used as the diazotizing agent, this reaction can be performed conveniently in an organic solvent such as ethanol, tetrahydrofuran, dioxane, acetonitrle, or acetic acid.

The diazonium salt (c) may also be produced by reacting the compound (d) with the same diazotizing agent as exemplified above in the presence of a fluorine-free acid such as hydrochloric acid, sulfuric acid, phosphoric acid or nitric acid, followed by reacting the diazonium salt with a fluorine-containing anion-yielding compound. For example, a diazonium compound (c) in which $A^\ominus$ is $BF_4^-$ can be easily produced by reacting the compound (d) with sodium nitrite in an aqueous hydrochloric acid solution to form the corresponding diazonium chloride derivative, and reacting it with tetrafluoroboric acid ($HBF_4$).

The diazonium salt (c) thus obtained, with or without isolation, is subjected to the aforesaid decomposition reaction to obtain the desired product [I].

The starting compound (d) used in process B may be produced, for example, by reacting ethyl 6-amino-7-chloro-1-ethyl-1,4-dihydro-4-oxo-1,8-naphthyridine-3-carboxylate described in YAKUGAKU ZASSHI (JAPAN), volume 99, No. 2, pp. 155-164 (February 1979) with the compound (b) in the same way as in Process A.

Process C: Acid or base treatment and reductive cleavage

The compounds of formula [I] are also obtained by treating a compound of the following formula

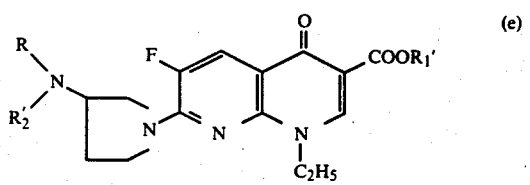

(e)

wherein
$R_1'$ is hydrogen or lower alkyl,
$R_2'$ is hydrogen or a protective group for the amino acid,
provided that $R_1'$ and $R_2'$ are not hydrogen at the same time, and
R is the same as defined above,
to treatment with an acid or base, and/or to reduction. The acid or base treatment and reductive treatment can be performed in the same way as described above with regard to Process A.

The starting compound (e) may be produced by, for example, using a compound of formula (a) in which $R_1$ is lower alkyl or a compound of formula (b) in which $R_2$ is an amino protective group in accordance with the displacement reaction in Process A.

The compounds of the present invention prepared in the above process can be isolated and purified by usual methods. The compounds [I] can be obtained in the free state or in the form of a salt depending upon the selection of the starting materials and the reaction conditions. The compounds [I] can be converted to pharmaceutically acceptable salts by treating them with an acid or a base. The acid may be a variety of organic and inorganic acids, examples of which are hydrochloric acid, acetic acid, lactic acid, succinic acid, lactobionic acid and methanesulfonic acid.

Examples of suitable bases are metal hydroxides such as sodium or potassium hydroxide, and metal carbonates such as sodium or potassium carbonate.

The novel 1,8-naphthyridine derivatives of this invention, as will be shown in Examples given hereinbelow, have excellent antibacterial activities and low toxicity. Accordingly, these compounds can be used as medicines for the treatment or prevention of bacterial infections of warmblooded animals including man.

The daily dosage of the compound [I] or its salt of this invention in administration to man should be adjusted according to the age, body weight and condition of a particular patient to be treated, the administration route, the number of administrations, etc. Usually, it is 1.6 to 120 mg/kg body weight/day, preferably 3 to 85 mg/kg body weight/day, for human adults and children. (Usually, the daily dosage for adults is 0.1 to 7 g, preferably 0.2 to 5 g.)

The compounds of this invention may be used as medicines, for example, in the form of pharmaceutical preparations containing them in admixture with an organic or inorganic pharmaceutically acceptable solid or liquid adjuvants suitable for oral or topical administration.

Pharmaceutically acceptable adjuvants are substances that do not react with the compounds of this invention. Examples are water, gelatin, lactose, starch, cellulose (preferably, microcrystalline cellulose), carboxymethyl cellulose, methyl cellulose, sorbitol, magnesium stearate, talc, vegetable oils, benzyl alcohol, gums, propylene glycol, polyalkylene glycols, methylparaben and other known medicinal adjuvants. The pharmaceutical preparations may be powder, granules, tablets, ointments, suppositories, creams, capsules, etc. They may be sterilized, and/or contain assistants such as preserving, stabilizing or wetting agents. They may further contain other therapeutically valuable substances according to the purpose of medication.

The pharmaceutical preparations of this invention, for examples tablets and capsules, may contain about 50 to 700 mg, generally 100 to 500 mg, of the compound of this invention, per tablet or capsule. These amounts are not critical, and may be varied according to whether the required amount of the compound of this invention is administered at one time or in divided doses.

The processes for producing the novel compounds [I] and their salts of the invention and their pharmacological activities are illustrated below.

Reference Example 1 shows a process for the preparation of the starting compound.

Examples 1 to 7 illustrate processes for the preparation of the compounds [I] or their salts of this invention.

Reference Example 2 shows a process for the preparation of a compound C which is new, and is outside the scope of this invention.

Examples A to C show the pharmacological activities of the compounds [I] and their salts of the invention in comparison with those of compounds outside the scope of the invention as controls.

Examples D and E show the preparations of pharmaceuticals containing the compounds [I] of this invention.

REFERENCE EXAMPLE 1

(1) Ethyl 1-ethyl-7-methoxy-1,4-dihydro-4-oxo-1,8-naphthyridine-3-carboxylate (82 g) was added to a mixture of fuming nitric acid (200 ml) and concd. sulfuric acid (330 ml), then the mixture was heated at 80° C. for 2 hours with stirring. The mixture was poured into 500 ml of ice-water. The precipitate was collected, washed with water, and dried. Recrystallization from ethanol gave 93.5 g of ethyl 1-ethyl-1,4-dihydro-7-methoxy-6-nitro-4-oxo-1,8-naphthyridine-3-carboxylate, m.p. 223.5°-227° C.

(2) A suspension of 20 g of ethyl 1-ethyl-1,4-dihydro-7-methoxy-6-nitro-4-oxo-1,8-naphthyridine-3-carboxylate in 400 ml of acetic acid was heated to 70° C. To this suspension was added portionwise 40 g of reduced iron-powder. The mixture was heated at 70° C. for one hour with stirring, and then 500 ml of ethanol was added. The mixture was filtered to remove the insoluble material and the solvent was distilled off under reduced pressure. To the residue was added 500 ml of water and the mixture was allowed to stand overnight in a refrigerator. The resulting precipitate was collected by filtration and recrystallized from ethanol to give 14.8 g of ethyl 6-amino-1-ethyl-1,4-dihydro-7-methoxy-4-oxo-1,8-naphthyridine-3-carboxylate, m.p. 250°-252° C.

(3) A solution of 12.0 g of ethyl 6-amino-1-ethyl-1,4-dihydro-7-methoxy-4-oxo-1,8-naphthyridine-3-carboxylate in 120 ml of ethanol and 60 ml of aqueous 42% tetrafluoroboric acid was cooled to 0° C. To the solution kept at 0°-3° C. was added 6.0 g of isoamyl nitrite. The mixture was stirred for 30 minutes at the same temperature, and then diluted with 600 ml of ether to give a precipitate which was collected and washed with ether to give 12.8 g of 3-ethoxycarbonyl-1-ethyl-1,4-dihydro-7-methoxy-4-oxo-1,8-naphthyridine-6-diazonium tetrafluoroborate, decomposing at 142°-147° C.

(4) A suspension of 10 g of 3-ethoxycarbonyl-1-ethyl-1,4-dihydro-7-methoxy-4-oxo-1,8-naphthyridine-6-diazonium tetrafluoroborate in 300 ml of xylene was heated under reflux for 30 minutes. After evaporation of the xylene, the residue was taken up in chloroform. The chloroform solution was washed with water and the solvent was distilled off. The crude product was chromatographed on silica gel with chloroform as an eluent to give 3.6 g of ethyl 1-ethyl-6-fluoro-1,4-dihydro-7-methoxy-4-oxo-1,8-naphthyridine-3-carboxylate, m.p. 181°-182° C.

(5) A suspension of 3.0 g of ethyl 1-ethyl-6-fluoro-1,4-dihydro-7-methoxy-4-oxo-1,8-naphthyridine-3-carboxylate in 40 ml of 10% sodium hydroxide was heated under reflux for 2 hours with stirring. The mixture was acidified with 20% hydrochloric acid to give 2.3 g of 1-ethyl-6-fluoro-1,4-dihydro-7-hydroxy-4-oxo-1,8-naphthyridine-6-carboxylic acid, m.p. above 300° C.

(6) A mixture containing 16 g of 1-ethyl-6-fluoro-7-hydroxy-1,4-dihydro-4-oxo-1,8-naphthyridine-3-carboxylic acid and 160 ml of phosphoryl chloride was heated under reflux for 20 minutes with stirring. After evaporation of excess phosphoryl chloride under reduced pressure, the residue was triturated with ice-water and the mixture was stirred for 20 minutes. The resulting precipitate was collected by filtration, washed with water, dried, and recrystallized from acetonitrile to give 14 g of 7-chloro-1-ethyl-6-fluoro-1,4-dihydro-4-oxo-1,8-naphthyridine-3-carboxylic acid, m.p. 265°-267° C.

EXAMPLE 1

A mixture containing 7-chloro-1-ethyl-6-fluoro-1,4-dihydro-4-oxo-1,8-naphthyridine-3-carboxylic acid (2.7 g), triethylamine (1.01 g), 3-acetylaminopyrrolidine (2.56 g), and acetonitrile (100 ml) was heated under reflux for 2 hours. The mixture was concentrated to dryness under reduced pressure. The residue was mixed with water, neutralized with acetic acid, and cooled. The precipitate was collected, washed successively with water and ethanol, and dried to give 3.2 g of 7-(3-acetylamino-1-pyrrolidinyl)-1-ethyl-6-fluoro-1,4-dihydro-4-oxo-1,8-naphthyridine-3-carboxylic acid, m.p. 283°-284° C., on recrystallization from dimethylformamide-ethanol.

(a) A mixture of 7-(3-acetylamino-1-pyrrolidinyl)-1-ethyl-6-fluoro-1,4-dihydro-4-oxo-1,8-naphthyridine-3-carboxylic acid (1.81 g) in 20% hydrochloric acid (20 ml) was heated under reflux for 3 hours with stirring. The mixture was concentrated to dryness under reduced pressure and then ethanol was added to the residue. After cooling the mixture, the resulting solid was collected and recrystallized from ethanol-water to yield 1.64 g of 7-(3-amino-1-pyrrolidinyl)-1-ethyl-6-fluoro-1,4-dihydro-4-oxo-1,8-naphthyridine-3-carboxylic acid hydrochloride (Compound 1), m.p. 285°–290° C. (decomp.).

(b) A solution of 7-(3-acetylamino-1-pyrrolidinyl)-1-ethyl-6-fluoro-1,4-dihydro-4-oxo-1,8-naphthyridine-3-carboxylic acid (0.88 g) in 10% sodium hydroxide (15 ml) was heated to reflux for 5 hours with stirring. The solution was neutralized with 20% hydrochloric acid to give a precipitate, which was collected, washed successively with water and ethanol, dissolved in 10% acetic acid, and adjusted to pH 7.5–8.0 with 10% aqueous ammonia. There were obtained 0.70 g of 7-(3-amino-1-pyrrolidinyl)-1-ethyl-6-fluoro-1,4-dihydro-4-oxo-1,8-naphthyridine-3-carboxylic acid, m.p. 259°–262° C. (decomp.).

EXAMPLE 2

In place of 3-acetylaminopyrrolidine, 3-benzyloxycarbonylaminopyrrolidine was allowed to react with 7-chloro-1-ethyl-6-fluoro-1,4-dihydro-4-oxo-1,8-naphthyridine-3-carboxylic acid in the same manner as described in Example 1 to give 7-(3-benzyloxycarbonylamino-1-pyrrolidinyl)-1-ethyl-6-fluoro-1,4-dihydro-4-oxo-1,8-naphthyridine-3-carboxylic acid, which was used in the next step:

(a) A solution of the compound thus prepared (0.908 g) in 10% sodium hydroxide (10 ml) was heated at 70°–80° C. for 1.5 hours with stirring. The reaction mixture was neutralized with 10% hydrochloric acid and the resulting precipitate was collected, washed successively with water and ethanol, then dried. There was obtained 0.60 g of 7-(3-amino-1-pyrrolidinyl)-1-ethyl-6-fluoro-1,4-dihydro-4-oxo-1,8-naphthyridine-3-carboxylic acid, m.p. 259°–262° C. (decomp.).

(b) A suspension of 7-(3-benzyloxycarbonylamino-1-pyrrolidinyl)-1-ethyl-6-fluoro-1,4-diyydro-4-oxo-1,8-naphthyridine-3-carboxylic acid (1.36 g) in acetic acid (50 ml) was vigorously shaken with 5% palladium-charcoal (136 mg) under hydrogen atmosphere. After the absorption of hydrogen ceased, the mixture was filtered to remove the palladium-charcoal and the filtrate was concentrated to dryness under reduced pressure. The residue was diluted with water and adjusted to pH 8 with 10% ammonia to give a precipitate, which was collected and dried to give 0.797 g of 7-(3-amino-1-pyrrolidinyl)-1-ethyl-6-fluoro-1,4-dihydro-4-oxo-1,8-naphthyridine-3-carboxylic acid, m.p. 259°–262° C. (decomp.).

EXAMPLE 3

A mixture containing 7-chloro-1-ethyl-6-fluoro-1,4-dihydro-4-oxo-1,8-naphthyridine-3-carboxylic acid (2.7 g), triethylamine (1.01 g), 3-aminopyrrolidine (1.72 g), and acetonitrile (100 ml) was heated under reflux for 1.5 hours. After cooling the mixture, the resulting precipitate was collected and suspended in water (20 ml). The suspension was adjusted to pH 7.5–8.0 with acetic acid. The precipitate was collected, washed with water, and dried to yield 2.85 g of 7-(3-amino-1-pyrrolidinyl)-1-ethyl-6-fluoro-1,4-dihydro-4-oxo-1,8-naphthyridine-3-carboxylic acid, m.p. 259°–262° C. (decomp.).

EXAMPLE 4

A mixture containing 7-chloro-1-ethyl-6-fluoro-1,4-dihydro-4-oxo-1,8-naphthyridine-3-carboxylic acid (5.41 g), 3-(N-acetylmethylamino)pyrrolidine (4.26 g), triethylamine (6.06 g), and ethanol (100 ml) was heated under reflux for 2 hours with stirring. The reaction mixture was concentrated to dryness under reduced pressure. To the residue was added water (70 ml) and acetic acid (15 ml). After cooling the mixture, the precipitate was collected, washed with water, and recrystallized from dimethylformamide. There were obtained 7.4 g of 7-[3-(N-acetylmethylamino)-1-pyrrolidinyl]-1-ethyl-6-fluoro-1,4-dihydro-4-oxo-1,8-naphthyridine-3-carboxylic acid, m.p. 287°–289° C.

The N-acetylmethylamino compound (3.0 g) thus prepared was dissolved in 10% sodium hydroxide (30 ml). The solution was heated to reflux for 6 hours and then adjusted to pH 7–8 with acetic acid. The precipitate was collected, washed with water, and dissolved in 1 N sodium hydroxide. The solution was adjusted again to pH 7–8 with acetic acid to give a precipitate, which was collected, washed with water, and dried. There were obtained 1.92 g of 1-ethyl-6-fluoro-1,4-dihydro-7-(3-methylamino-1-pyrrolidinyl)-4-oxo-1,8-naphthyridine-3-carboxylic acid, m.p. 242°–242.5° C.

The methylamino compound (1.0 g) thus obtained was dissolved in 1 N hydrochloric acid (5 ml). To the hot solution was added 45 ml of ethanol and the mixture was cooled. The resulting precipitate was collected and dried to give 0.97 g of 1-ethyl-6-fluoro-1,4-dihydro-7-(3-methylamino-1-pyrrolidinyl)-4-oxo-1,8-naphthyridine-3-carboxylic acid hydrochloride (Compound 2), m.p. about 270° C. (decomp.).

3-(N-Acetyl-n-propylamino)pyrrolidine was allowed to react with 7-chloro-1-ethyl-6-fluoro-1,4-dihydro-4-oxo-1,8-naphthyridine-3-carboxylic acid in the same manner as described above and yield 7-[3-(N-acetyl-n-propylamino)-1-pyrrolidinyl]-1-ethyl-6-fluoro-1,4-dihydro-4-oxo-1,8-naphthyridine-3-carboxylic acid. Subsequent hydrolysis of this compound with hydrochloric acid gave 1-ethyl-6-fluoro-1,4-dihydro-4-oxo-7-(3-N-propylamino-1-pyrrolidinyl)-1,8-naphthyridine-3-carboxylic acid hydrochloride, m.p. about 270° C. (decomp.).

EXAMPLE 5

A mixture containing ethyl 7-chloro-1-ethyl-6-fluoro-1,4-dihydro-4-oxo-1,8-naphthyridine-3-carboxylate (2.99 g), 3-(N-acetylmethylamino)pyrrolidine (2.13 g), triethylamine (1.52 g), and chloroform (30 ml) was heated to reflux for 4 hours with stirring. After cooling the mixture, 5% hydrochloric acid (20 ml) was added with stirring. The chloroform layer was separated off and the solvent was evaporated. To the residue was added 20 ml of acetonitrile and the mixture was cooled. The resulting precipitate was collected and recrystallized from acetonitrile to give 3.51 g of ethyl 7-[3-(N-acetylmethylamino)-1-pyrrolidinyl]-1-ethyl-6-fluoro-1,4-dihydro-4-oxo-1,8-naphthyridine-3-carboxylate, m.p. 212°–213° C.

A solution of 2.02 g of the compound thus prepared in 20 ml of 10% sodium hydroxide was heated to reflux for 6 hours with stirring. The mixture was worked up as described in Example 4 to give 1.22 g of 1-ethyl-6-fluoro-1,4-dihydro-7-(3-methylamino-1-pyrrolidinyl)-4-oxo-1,8-naphthyridine-3-carboxylic acid, m.p. 242°–242.5° C.

EXAMPLE 6

A mixture containing ethyl 1-ethyl-7-ethylsulfonyl-6-fluoro-1,4-dihydro-4-oxo-1,8-naphthyridine-3-carboxylate (1.78 g), 3-(N-acetylmethylamino)pyrrolidine (2.13 g), and acetonitrile (70 ml) was heated under reflux for 3 hours. After cooling the mixture, the resulting precipitate was collected and recrystallized from acetonitrile to yield 1.58 g of ethyl 7-[3-(N-acetylmethylamino)-1-pyrrolidinyl]-1-ethyl-6-fluoro-1,4-dihydro-4-oxo-1,8-naphthyridine-3-carboxylate, m.p. 212°–213° C.

The compound thus obtained was hydrolyzed by treating with hydrochloric acid in the same manner as described in Example (1a). There was obtained 1-ethyl-6-fluoro-1,4-dihydro-7-(3-methylamino-1-pyrrolidinyl)-4-oxo-1,8-naphthyridine-3-carboxylic acid hydrochloride (Compound 2), m.p. ca. 270° C. (decomp.).

EXAMPLE 7

To a solution, maintained at 0°–3° C., of ethyl 7-(3-acetylamino-1-pyrrolidinyl)-6-amino-1-ethyl-1,4-dihydro-4-oxo-1,8-naphthyridine-3-carboxylate (3.59 g) in 1 N hydrochloric acid (70 ml) was gradually added a solution of sodium nitrite (0.90 g) in 11 ml of water with stirring. Aqueous hexafluorophosphoric acid (65%) was added to this solution until formation of a diazonium salt was complete. The precipitate was collected and dried to give 4.7 g of the diazonium salt.

The diazonium salt (4 g) was suspended in 150 ml of toluene and the suspension was heated at 80°–100° C. for 15 minutes with stirring. The resulting precipitate was collected and mixed with water. The aqueous mixture was extracted with chloroform. The extract was dried, and the chloroform was distilled off. The crystalline solid was collected and recrystallized from methanol-ethyl acetate to give 1.77 g of ethyl 7-(3-acetylamino-1-pyrrolidinyl)-1-ethyl-6-fluoro-1,4-dihydro-4-oxo-1,8-naphthyridine-3-carboxylate, m.p. 266°–269° C.

A mixture of the compound (1.5 g) thus prepared and 20% hydrochloric acid (7.5 ml) was heated to reflux for 3 hours. The mixture was concentrated to dryness under reduced pressure. To the residue was added 10 ml of ethanol. The resulting solid was collected, and dissolved in 5 ml of water. The solution was treated with 0.1 g of charcoal, and filtered. To the filtrate was added 8 ml of ethanol and the mixture was cooled in an ice bath to give 1.2 g of 7-(3-amino-1-pyrrolidinyl)-1-ethyl-6-fluoro-1,4-dihydro-4-oxo-1,8-naphthyridine-3-carboxylic acid hydrochloride (Compound 1), m.p. 285°–290° C. (decomp.).

REFERENCE EXAMPLE 2

A mixture containing 7-chloro-1-ethyl-6-fluoro-1,4-dihydro-4-oxo-1,8-naphthyridine-3-carboxylic acid (1.0 g), pyrrolidine (1.31 g), and acetonitrile (80 ml) was heated under reflux for 2 hours. The reaction mixture was concentrated to dryness under reduced pressure. The residue was mixed with 5% hydrochloric acid (25 ml) and the mixture was heated on a steam-bath for several minutes and then cooled. The resulting precipitate was collected, washed with water, and recrystallized from chloroform-ethyl acetate to give 1.0 g of 1-ethyl-6-fluoro-1,4-dihydro-4-oxo-7-(1-pyrrolidinyl)-1,8-naphthyridine-3-carboxylic acid, m.p. 299°–300° C.

EXAMPLE A

The minimum inhibitory concentrations (MIC, μg/ml) of the following compounds in vitro were measured by the agar dilution method of [Chemotherapy, Vol. 22, No. 16, page 1126 (1974)]. The results are shown in Table 1.
Compound 1

7-(3-Amino-1-pyrrolidinyl)-1-ethyl-6-fluoro-1,4-dihydro-4-oxo-1,8-naphthyridine-3-carboxylic acid hydrochloride

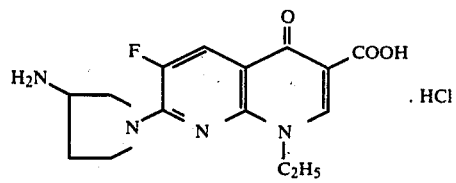

Compound 2
1-Ethyl-6-fluoro-1,4-dihydro-7-(3-methylamino-1-pyrrolidinyl)-4-oxo-1,8-naphthyridine-3-carboxylic acid hydrochloride

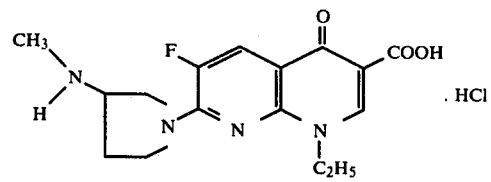

Compound A
1-Ethyl-1,4-dihydro-4-oxo-7-(1-pyrrolidinyl)-1,8-naphthyridine-3-carboxylic acid (the compound disclosed in Japanese Laid-Open Patent Publication No. 126697/74)

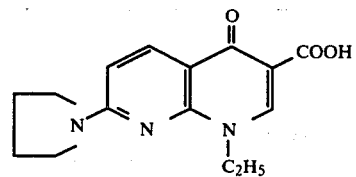

Compound B
6-Chloro-1-ethyl-1,4-dihydro-4-oxo-7-(1-pyrrolidinyl)-1,8-naphthyridine-3-carboxylic acid [the compound disclosed in YAKUGAKU ZASSHI (JAPAN) 99 (2), 155–156 (February 1979)]

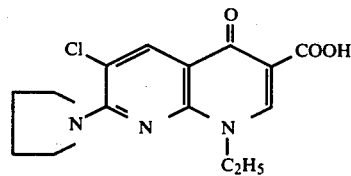

Compound C
1-Ethyl-6-fluoro-1,4-dihydro-4-oxo-7-(1-pyrrolidinyl)-1,8-naphthyridine-3-carboxylic acid (the compound obtained by the procedure described in Reference Example 2)

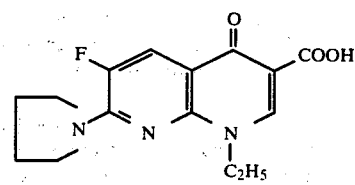

Compound D
1-Ethyl-1,4-dihydro-7-methyl-4-oxo-1,8-naphthyridine-3-carboxylic acid (Nalidixic acid) (the compound disclosed in U.S. Pat. No. 3,149,104)

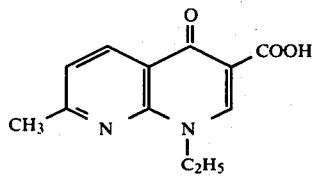

Compound E
8-Ethyl-5,8-dihydro-5-oxo-2-(1-pyrrolidinyl)-pyrido[2,3-d]pyrimidine-6-carboxylic acid (Piromidic acid) (the compound disclosed in U.S. Pat. No. 3,770,742)

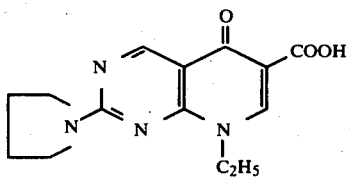

ative), Compound B (6-chloro-1,8-naphthyridine derivative), and Compounds D and E which are commercially available synthetic antibacterial agents.

EXAMPLE B (In vivo therapeutic efficacy)

Compounds 1, 2 and C were each dissolved in deionized water or suspended in a 0.2% aqueous solution of CMC. Each of the solutions was orally administered to mice infected with each of test organisms under the conditions described below, and the medium effective doses ($ED_{50}$) obtained are shown in Table II.

Experimental Conditions

Mice:
  Male mice (ddY) weighing about 20 g
Infection:
  (1) *Staphylococcus aureus* No. 50774:
    Intravenous infection with about $5 \times 10^8$ cells per mouse suspended in saline.
  (2) *Streptococcus pyogenes* 65-A:
    Intraperitoneal infection with about $3 \times 10^7$ cells per mouse suspended in barin heart infusion broth.
  (3) *Escherichia coli* P-5101:
    Intraperitoneal infection with about $9 \times 10^6$ cells per mouse suspended in trypto-soy broth with

TABLE I

| | In vitro antibacterial activity against 22 strains of bacteria | | | | | | |
|---|---|---|---|---|---|---|---|
| | Compound | | | | | | |
| Bacteria | 1 | 2 | A | B | C | D | E |
| Gram-positive bacteria | | | | | | | |
| *Staphylococcus epidermidis* No. 8 | 0.2 | 0.39 | 3.13 | 3.13 | 0.39 | 25 | 12.5 |
| *Staphylococcus aureus* No. 80 | 0.39 | 0.78 | 3.13 | 6.25 | 0.2 | 25 | 12.5 |
| *Staphylococcus aureus* Smith | 0.39 | 0.78 | 6.25 | 6.25 | 0.39 | 25 | 12.5 |
| *Staphylococcus aureus* 209P JC-1 | 0.2 | 0.78 | 12.5 | 12.5 | 0.39 | 100 | 12.5 |
| *Staphylococcus aureus* No. 50774 | 0.2 | 0.78 | 6.25 | 6.25 | 0.2 | 50 | 12.5 |
| *Streptococcus faecalis* P-2473 | 3.13 | 6.25 | >200 | >200 | 6.25 | >200 | >200 |
| *Streptococcus pyogenes* 65A | 1.56 | 3.13 | >200 | 50 | 3.13 | >200 | 200 |
| *Corynebacterium pyogenes* C-21 | 0.39 | 1.56 | >200 | 50 | 0.78 | >200 | 25 |
| Gram-negative bacteria | | | | | | | |
| *Escherichia coli* NIHJ JC-2 | 0.2 | 0.2 | 25 | 50 | 1.56 | 12.5 | 25 |
| *Escherichia coli* P-5101 | 0.1 | 0.2 | 50 | 50 | 0.78 | 3.13 | 12.5 |
| *Escherichia coli* P-140a | <0.05 | 0.1 | 3.13 | 50 | 0.78 | 1.56 | 12.5 |
| *Salmonella typhimurium* S-9 | 0.1 | 0.2 | 50 | 50 | 0.78 | 3.13 | 25 |
| *Salmonella enteritidis* No. 1891 | 0.1 | 0.1 | 6.25 | 25 | 0.39 | 3.13 | 25 |
| *Shigella flexneri* 2a | 0.1 | 0.2 | >200 | 50 | 1.56 | 6.25 | 12.5 |
| *Shigella flexneri* 4a P-330 | 0.1 | 0.1 | 6.25 | >100 | 3.13 | 3.13 | 12.5 |
| *Klebsiella pneumoniae* No. 13 | 0.2 | 0.39 | >200 | >100 | 1.56 | 12.5 | 25 |
| *Enterobacter cloacae* P-2540 | <0.05 | 0.39 | >200 | 50 | 1.56 | 6.25 | 25 |
| *Pseudomonas aeruginosa* Tsuchiijima | 0.78 | 0.78 | >200 | >100 | 3.13 | 200 | 100 |
| *Pseudomonas aeruginosa* No. 12 | 0.78 | 1.56 | >200 | >100 | 3.13 | 200 | 100 |
| *Serratia marcescens* IFO 3736 | 0.39 | 1.56 | >200 | >100 | 3.13 | 6.25 | 50 |
| *Proteus morganii* Kono | 0.2 | 0.39 | >200 | >100 | 1.56 | 6.25 | 25 |
| *Proteus mirabilis* P-2381 | 0.39 | 1.56 | >200 | >100 | 6.56 | 6.25 | 50 |

The following can be seen from the results shown in Table I.

(1) Compounds 1 and 2 of this invention exhibit very high antibacterial activities against Gram-positive and Gram-negative bacteria including *Pseudomonas aeruginosa*.

(2) Compounds 1 and 2 of this invention exhibit far better in vitro antibacterial activity against Gram-negative bacteria, including *Pseudomonas aeruginosa*, than Compound A (6-unsubstituted-1,8-naphthyridine deriv- 4% mucin.

(4) *Pseudomonas aeruginosa* No. 12:
  Intraperitoneal infection with about $5 \times 10^3$ cells per mouse suspended in trypto-soy broth with 4% mucin.
Medication:
  Twice, about 5 minutes and 6 hours after infection.
Observation:

| Staphylococcus aureus No. 50774 | for 14 days |
| Streptococcus pyogenes 65-A | |
| Escherichia coli P-5101 | for 7 days |
| Pseudomonas aeruginosa No. 12 | |

TABLE II

In vivo efficacy against systemic infections in mice

| Compound | Staphylococcus aureus No. 50774 | Streptococcus pyogenes 65-A | Escherichia coli P-5101 | Pseudomonas aeruginosa No. 12 |
| --- | --- | --- | --- | --- |
| | Route | | | |
| | po | po | po | po |
| 1 | 3.0 | 21.0 | 1.7 | 3.7 |
| 2 | 4.8 | 42.0 | 1.4 | 6.5 |
| C | — | — | >50 | >100 |

Note:
The numerals in the table show $ED_{50}$ (mg/kg). $ED_{50}$ values were calculated in accordance with the Behrens-Kaerber method (Arch. Exp. Path. Pharm., 162, 480 (1931)).
po: oral administration.

The following conclusions can be drawn from the results shown in Table II.

(1) Compounds 1 and 2 of this invention show potent therapeutic effects on systemic infections with Gram-positive bacteria and Gram-negative bacteria.

(2) Compounds 1 and 2 of this invention exhibit better therapeutic effects against systemic infections with Gram-negative bacteria, including *Pseudomonas aeruginosa*, than Compound C (6-fluoro-1,8-naphthyridine derivative).

EXAMPLE C (Acute toxicity)

A solution containing each of Compounds 1 and 2 of this invention in various concentrations was orally given to male mice (ddY) at a dose of 0.1 ml per 10 g of body weight. The number of dead mice was counted after 7 days, and the value of median lethal dose ($LD_{50}$, mg/kg) was calculated in accordance with the Behrens-Kaerber method. The results are shown in Table III.

TABLE III

| Acute oral toxicity in mice | |
| --- | --- |
| Compound | $LD_{50}$ (mg/kg) |
| 1 | >2,000 |
| 2 | >2,000 |

From the results shown in Table III it is seen that the compounds 1 and 2 of this invention have low oral toxicity.

EXAMPLE D

| Compound 1 or 2 | 250 g |
| --- | --- |
| Starch | 50 g |
| Lactose | 35 g |
| Talc | 15 g |

The above components were blended and granulated and filled into 1,000 capsules in accordance with conventional methods.

EXAMPLE E

| Compound 1 or 2 | 250 g |
| --- | --- |
| Starch | 54 g |
| Calcium carboxymethyl cellulose | 40 g |
| Microcrystalline cellulose | 50 g |
| Magnesium stearate | 6 g |

The above components were blended, granulated and made into tablets in a manner known per se. Thus, 1,000 tablets each weighing 400 mg were formed.

What we claim is:

1. A 1,8-naphthyridine compound of the formula

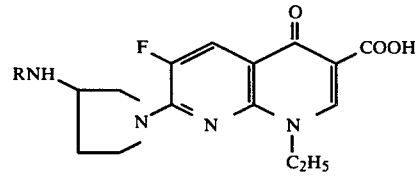

wherein R is hydrogen, methyl, ethyl or propyl, or a nontoxic pharmaceutically acceptable salt thereof.

2. 7-(3-Amino-1-pyrrolidinyl)-1-ethyl-6-fluoro-1,4-dihydro-4-oxo-1,8-naphthyridine-3-carboxylic acid or a nontoxic pharmaceutically acceptable salt thereof.

3. A compound according to claim 2 wherein the salt is a hydrochloride.

4. 1-Ethyl-6-fluoro-1,4-dihydro-7-(3-methylamino-1-pyrrolidinyl)-4-oxo-1,8-naphthyridine-3-carboxylic acid or a nontoxic pharmaceutically acceptable salt thereof.

5. A compound according to claim 4 wherein the salt is a hydrochloride.

6. An antibacterial composition comprising as an active ingredient an antibacterially effective amount of a 1,8-naphthyridine compound defined in claim 1 and a pharmaceutically acceptable carrier therefor.

7. A method for treatment of a bacterial infection which comprises administering to a warm-blood animal an antibacterially effective amount of a naphthyridine compound defined in claim 1.

* * * * *